(12) United States Patent
Libert et al.

(10) Patent No.: US 9,828,437 B2
(45) Date of Patent: Nov. 28, 2017

(54) MMP8 INACTIVATING ANTIGEN BINDING PROTEINS

(75) Inventors: Claude Libert, Oudenaarde (BE); Eline Dejonckheere, De-Pimte, Sint-Denijs-Westrem (BE); Roosmarijn Vandenbroucke, Dentergem (BE)

(73) Assignees: VIB vzw, Ghent (BE); Universiteit Gent, Ghent (BE)

( * ) Notice: Subject to any disclaimer, the term of this patent is extended or adjusted under 35 U.S.C. 154(b) by 1227 days.

(21) Appl. No.: 13/883,444

(22) PCT Filed: Nov. 2, 2011

(86) PCT No.: PCT/EP2011/069238
§ 371 (c)(1),
(2), (4) Date: Oct. 24, 2013

(87) PCT Pub. No.: WO2012/059513
PCT Pub. Date: May 10, 2012

(65) Prior Publication Data
US 2014/0037646 A1 Feb. 6, 2014

(30) Foreign Application Priority Data
Nov. 4, 2010 (GB) .................................. 1018602.1

(51) Int. Cl.
C07K 16/40 (2006.01)

(52) U.S. Cl.
CPC .......... *C07K 16/40* (2013.01); *C07K 2317/22* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| 5,736,341 A | 4/1998 | Sorsa et al. |
| 6,686,355 B2 | 2/2004 | Barvian et al. |
| 2002/0155113 A1 | 10/2002 | Chun et al. |
| 2006/0211088 A1* | 9/2006 | Hermans ................ C07K 16/00 435/69.1 |

FOREIGN PATENT DOCUMENTS

| WO | 9404678 A1 | 3/1994 |
| WO | 9607103 A1 | 3/1996 |
| WO | 9633172 A1 | 10/1996 |
| WO | 9749805 A2 | 12/1997 |
| WO | 0162261 A1 | 8/2001 |
| WO | 2007118670 A1 | 10/2007 |
| WO | 2010066740 A1 | 6/2010 |
| WO | 2012059513 A1 | 5/2012 |

OTHER PUBLICATIONS

S. Sadallah et al., "Elastase and metalloproteinase activities regulate soluble complement receptor 1 release." European Journal of Immunology. vol. 29. No. 11. Nov. 1999 (Nov. 1999). pp. 3754-3761.
K. Hasty et al., "Heterogeneity among human collagenases demonstrated by monoclonal antibody that selectively recognizes and inhibits human neutrophil collagenase." The Journal of Experimental Medicine. vol. 159. No. 5. May 1, 1984 (May 1, 1984). pp. 1455-1463.
A. Folgueras et al., "Collagenase-2 deficiency or inhibition impairs experimental autoimmune encephalomyelitis in mice." The Journal of Biological Chemistry. vol. 283. No. 14. Apr. 4, 2008 (Apr. 4, 2008). pp. 9465-9474.
PCT International Search Report, PCT/EP2011/069238, dated Jan. 20, 2012.

* cited by examiner

*Primary Examiner* — Sharon X Wen
(74) *Attorney, Agent, or Firm* — TraskBritt, P.C.

(57) ABSTRACT

Described are MMP8 inactivating antigen binding proteins, such as antigen binding proteins comprising an amino acid sequence that comprises 4 framework regions and 3 complementary determining regions; further described is the use of such antigen binding proteins to treat inflammation, such as, but not limited to, systemic inflammatory response syndrome, sepsis, LPS induced inflammation, renal ischemia/reperfusion injury, ventilation induced lung injury, periodontal inflammation, rheumatoid arthritis, multiple sclerosis, ankylosing spondylitis, Lyme arthritis and osteoarthritis.

7 Claims, 6 Drawing Sheets

MMP8 INACTIVATING ANTIGEN BINDING PROTEINS

CROSS-REFERENCE TO RELATED APPLICATION

This application is a national phase entry under 35 U.S.C. §371 of International Patent Application PCT/EP2011/069238, filed Nov. 2, 2011, designating the United States of America and published in English as International Patent Publication WO2012/059513 A1 on May 10, 2012, which claims the benefit under Article 8 of the Patent Cooperation Treaty to United Kingdom Application Serial No. 1018602.1, filed Nov. 4, 2010.

TECHNICAL FIELD

The disclosure relates generally to biotechnology and, more particularly, to MMP8 inactivating antigen binding proteins, such as antigen binding proteins comprising an amino acid sequence (or peptide) that comprises 4 framework regions and 3 complementary determining regions; it relates further to the use of such antigen binding proteins to treat inflammation, such as, but not limited to, systemic inflammatory response syndrome, sepsis, LPS induced inflammation, renal ischemia/reperfusion injury, ventilation induced lung injury, periodontal inflammation, rheumatoid arthritis, multiple sclerosis, ankylosing spondylitis, Lyme arthritis and osteoarthritis.

BACKGROUND

"Systemic Inflammatory Response Syndrome" (SIRS) occurs when the body's response to an insult is an uncontrolled, systemic inflammatory response. Death is caused by the exaggerated reaction rather than by the insult itself (Cohen, 2002). SIRS is diagnosed when the patient shows two or more of the following clinical findings: fever, increased heart or respiratory rate, and aberrant white blood cell count. SIRS can be caused by a sterile trigger, for instance, burns, hemorrhage, trauma, or by bacterial, viral or fungal infection. It is termed severe SIRS when there is organ failure, and if the patient has persistent hypotension despite fluid resuscitation, the condition is known as shock. In the presence of infection, it is known as sepsis, which can proceed to severe sepsis and septic shock.

SIRS remains one of the leading causes of death in intensive care units (ICUs) worldwide. About 750,000 cases of severe sepsis occur in the United States every year (Agnus et al., 2001) and this number will continue to rise as the population ages further and co-morbidities, such as, infarctions, alcohol abuse and obesity increase (Esper et al., 2006). One-fifth of patients in intensive care have sepsis, and mortality rate among severe sepsis patients is over 30% (Agnus et al., 2001).

Despite intensive research into SIRS pathology for the past decades, only a few new therapies have emerged, and current treatments remain mostly supportive. Treatments can aim to prevent infection or to treat it with antibiotics, and to cope with organ dysfunction and failure by supportive therapy, such as, fluid resuscitation, kidney dialysis, vasopressor administration and mechanical ventilation (van Ruler et al., 2009). Hardly any therapy deals with the host response, which is the underlying cause of the condition. The newest approved treatment strategy, the use of recombinant human activated protein C (Vincent, 2007), is subject to criticism. The lack of effective treatment, high prevalence rate, high mortality rate, high economic costs and rapidity by which antibiotics resistance develops all underscore the need for further extensive studies into SIRS pathology.

"Matrix Metallo-Proteinase" (MMP) activity was initially discovered in 1962 as a collagenolytic activity in the tail of tadpoles during the degradation of extracellular matrix (ECM) proteins, which is required for metamorphosis (Gross and Lapiere, 1962). To date, the MMP family comprises 25 structurally and functionally related members, of which 24 can be found in Mammals (Parks et al., 2004). MMPs are characterized by a shared multidomain structure, and in particular, a highly conserved catalytic domain consisting of a zinc ($Zn^{2+}$)-binding consensus sequence. Another hallmark of MMPs is the activation of the inactive zymogen by the "cysteine switch," which interrupts the interaction between a cysteine in the prodomain and the $Zn^{2+}$ ion at the active site (Van Wart and Birkedal-Hansen, 1990). MMPs are important regulators of cellular activities: they collectively degrade all structural components of the ECM8 and thereby influence several physiological processes, including reproduction (Hulboy et al., 1997), embryogenesis (Vu and Werb, 2000), angiogenesis (Roy et al., 2006) and tissue remodeling (Page and McCaw, 2007). ECM degradation, besides facilitating cell migration, also leads to the release of bound signaling molecules, such as, chemokines, cytokines and growth factors. More recently, it has become widely agreed that MMPs also have a central role in the direct activation of signaling molecules, which proves that MMPs also contribute to various aspects of immunity (Cauwe et al., 2007). MMP activity is hardly detectable under normal physiological conditions, but it is evident during certain biological processes. Tight regulation occurs at the levels of transcription, activation of the zymogen, interaction with specific ECM components, and inhibition by endogenous inhibitors (Sternlight and Werb, 2001). Breakdown of the regulation of MMP activity could lead to diseases, such as, arthritis, tumor metastasis and fibrosis (Malemud, 2006).

Matrix metalloproteinase-8 (MMP8), also known as collagenase-2 or neutrophil collagenase, was originally believed to be expressed only by neutrophils. More recently, it has become clear that MMP8 can be expressed in a wide range of cells, such as, epithelial cells, fibroblasts and macrophages, mainly during inflammatory conditions (Van Lint and Libert, 2006). Inactive MMP8 is stored in the intracellular granules of neutrophils and is released upon activation to ensure rapid availability of MMP8 at inflammatory sites. The effect of MMP8 expression on cancer progression and its association with several inflammatory disorders has been described (Van Lint and Libert, 2006). Tester et al., (2007) described that $MMP8^{-/-}$ mice are no longer LPS responsive. As a consequence, MMP inhibitors in general, and MMP8 inhibitors particularly are claimed in the treatment of, amongst other, inflammation. WO9633172 discloses the use of arylsulfonyl hydroxamic derivatives as MMP inhibitors, and their use for treatment of sepsis and septic shock. U.S. Pat. No. 6,686,355 discloses the use of MMP inhibiting biphenyl sulfonamide derivatives to treat inflammation. WO0162261 describes the use of tetracycline based antibiotics to inhibit MMP1, MMP2, MMP8 or MMP9 in respiratory diseases. Small compound inhibitors, however, have the disadvantage to be cross reactive with several MMP's thereby causing unwanted side effects. Therefore, several researches tried to develop more specific inhibitors, including inactivating antibodies. Whereas several MMP specific antibodies have been described for detection and immunological staining of MMP's only few antibodies have been described with MMP inactivating activity, and no inactivating MMP8 antibody has been described.

SUMMARY OF THE DISCLOSURE

Surprisingly, we found that a camelid antibody derived nanobody, isolated against MMP8, showed MMP8 inactivating activity, and that nanobody can be used to treat SIRS, sepsis, septic shock, and TLR4 induced inflammation.

A first aspect hereof is a MMP8 inactivating antigen binding protein. "Inactivating," as used herein, means that the antigen significantly reduces the MMP8 activity when added in a 100/1 dilution, as measured in an ENZCHECK® fluorescein-labeled DQ gelatin conjugate test (Invitrogen). The antigen binding protein can be any antigen binding protein known to the person skilled in the art, such as, but not limited to, antibodies, heavy chain antibodies (hcAb), single domain antibodies (sdAb), variable domain of camelid heavy chain antibody (VHH) variable domain of the new antigen receptor (VNAR), engineered CH2 domains (nanoantibodies; Dimitrov, 2009), minibodies (Tramontano et al., 1994), and ALPHABODIES™ (WO2010066740). Preferably, the antigen binding protein comprises an amino acid sequence that comprises 4 framework regions (FR) and 3 complementary determining regions (CDR), according to Kabat. Binding domains comprising 4 FRs and 3 CDRs, preferably in a sequence FR1-CDR1-FR2-CDR2-FR3-CDR3-FR4, are known to the person skilled in the art and have been described, as a non-limiting example in Wesolowski et al., (2009). Even more preferably, the antigen binding protein is derived from a camelid antibody, such as from a heavy chain camelid antibodies, devoid of light chains, such as, a variable domain of heavy chain camelid antibody (VHH).

Camelid antibodies, and the VHH derived sequences are known to the person skilled in the art. Camelid antibodies have been described, amongst others in WO9404678 and in WO2007118670. Most preferably, the VHH comprises, preferably, consists of a sequence selected from the group consisting of SEQ ID NO:1 through SEQ ID NO:8.

A further aspect is a nucleic acid encoding a MMP8 inactivating antigen binding protein hereof A nucleic acid, as used herein, refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. In a preferred embodiment, the nucleic acid is operably linked to a promoter, thereby allowing expression of the MMP8 inactivating protein in a selected host. "Operably linked" refers to a juxtaposition wherein the components so described are in a relationship permitting them to function in their intended manner. A promoter sequence "operably linked" to a coding sequence is ligated in such a way that expression of the coding sequence is achieved under conditions compatible with the promoter sequence. "Promoter sequence," as used herein, refers to a functional DNA sequence unit that, when operably linked to a coding sequence and possibly placed in the appropriate inducing conditions, is sufficient to promote transcription of the coding sequence.

Still another aspect is a host cell, transformed with a vector comprising a nucleic acid hereof. The host cell can be any host cell known to the person skilled in the art and includes, but is not limited to bacterial cells, fungals cells including yeast cells, insect cells and mammalian cells. Preferably, the host cell is a bacterial cell or a yeast cell.

Still another aspect is the use of a host cell hereof, for the production of a MMP8 inactivating antigen binding protein. The production will normally comprise (a) the cultivation of the host cell (b) creating conditions allowing the expression of the nucleic acid encoding the MMP8 inactivating antigen binding protein—either in parallel with the cultivation or at the end of the cultivation (c) isolating the MMP8 inactivating binding protein. The MMP8 inactivating protein can be secreted in the medium, or it may remain intracellular, requiring disruption of the host cell for the isolation of the MMP8 inactivating protein.

Another aspect hereof is the use of an antigen binding protein hereof for the detection of MMP8. Detection, as used herein, can be qualitative or quantitative; it may be intended to localize MMP8 in a cell or in a tissue of an organism, or it may be used to measure expression in the cell or tissue.

Still another aspect hereof is the use of an MMP8 inactivating antigen binding protein hereof for treatment of an inflammatory disease. In one preferred embodiment, the inflammatory disease is a Toll-like receptor-4 (TLR4) mediated inflammatory disease. TLR4 mediated inflammatory diseases are known to the person skilled in the art and include, but are not limited to, systemic inflammatory response syndrome, sepsis, LPS induced inflammation and renal ischemia/reperfusion injury (Pulskens et al., 2008). In another preferred embodiment, the inflammatory disease is selected from the list of diseases consisting of systemic inflammatory response syndrome, sepsis, LPS induced inflammation, renal ischemia/reperfusion injury, ventilation induced lung injury, periodontal inflammation, rheumatoid arthritis, multiple sclerosis, ankylosing spondylitis, Lyme arthritis and osteoarthritis.

DETAILED DESCRIPTION AND EXAMPLES

Example 1

MMP-8$^{-/-}$ Mice are Protected Against LPS Lethal Shock

Figure 1A:
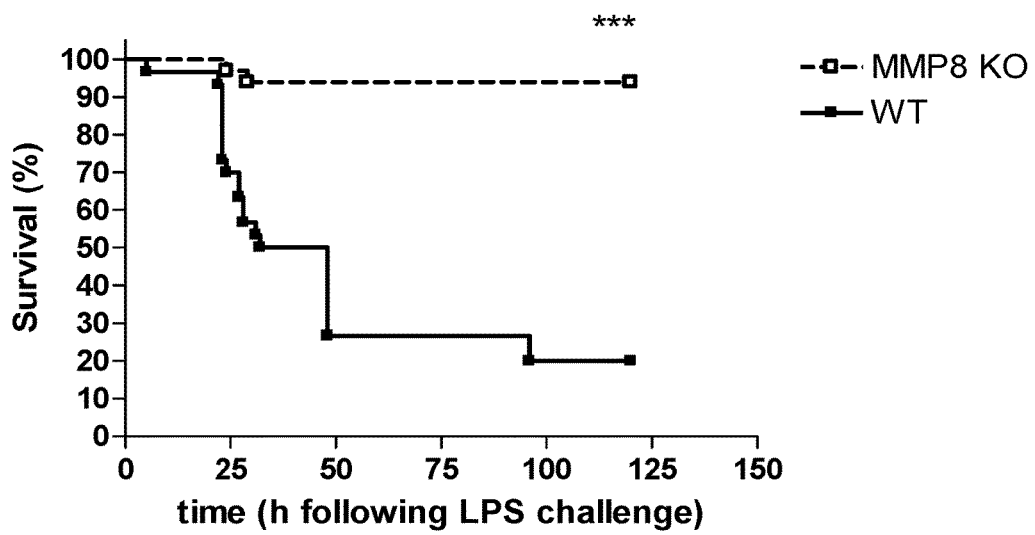
FIGS. 1A and 1B: survival (FIG. 1A) and evolution of the body temperature (FIG. 1B) of wild type and MMP8$^{-/-}$ mice treated with 350 μg LPS.
Figure 1B:
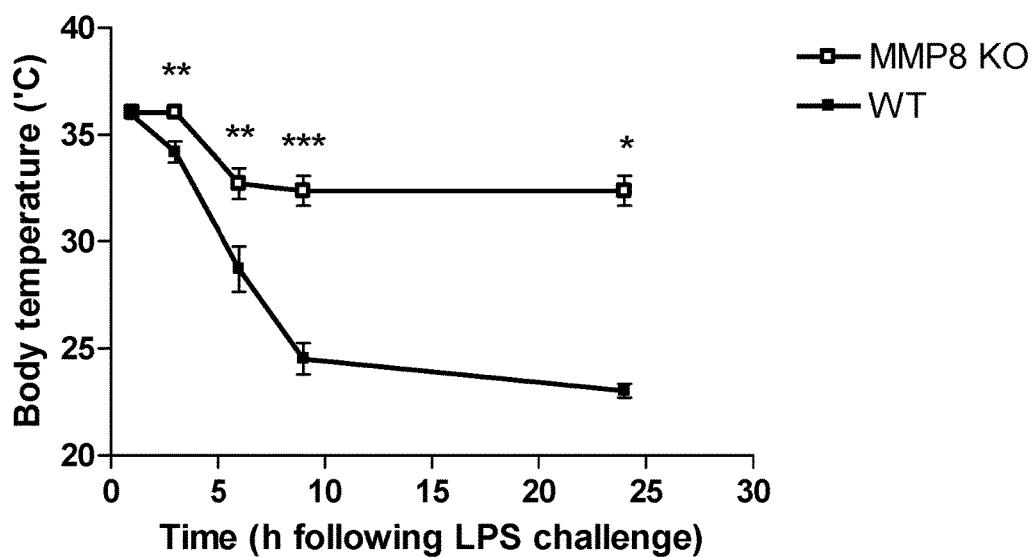

MMP-8$^{-/-}$ mice, with a C57BL/6J genetic background, and wild type mice were housed in an SPF animal facility. Both males and females (8-12 weeks old) were used. All experiments were approved by the ethics committee of Ghent University. Mice were injected intraperitoneally (i.p.) with 17.5 mg/kg body weight LPS from *Salmonella enterica* serotype abortus equi (Sigma Aldrich) to induce the endotoxemia model. MMP-8$^{-/-}$ mice were highly significantly protected against death (FIG. 1A) and hypothermia (FIG. 1B) induced by LPS challenge.

Example 2

MMP-8$^{-/-}$ Mice Show Reduced Sensitivity to Renal Ischemia/Reperfusion

Figure 2A:
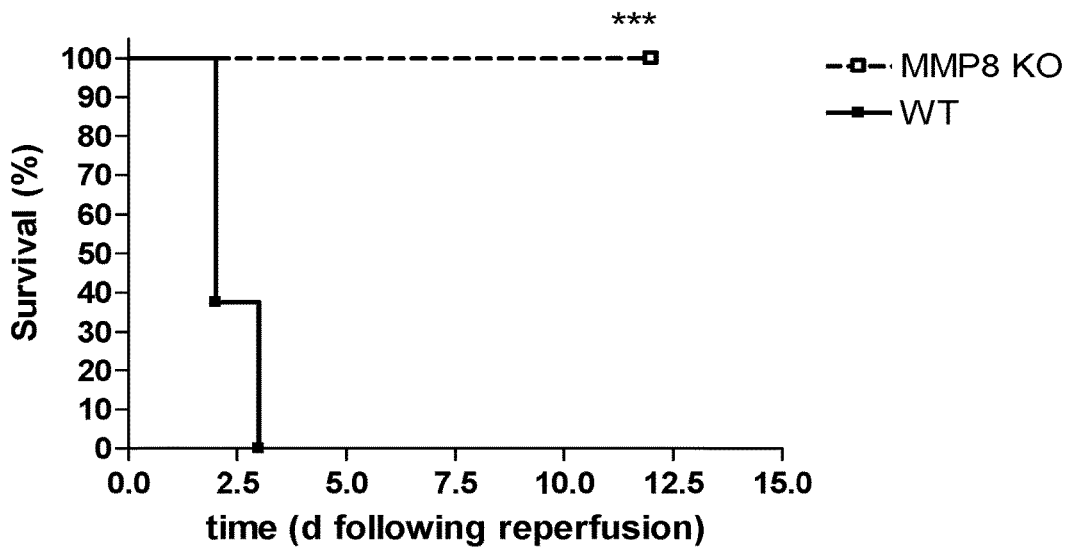
FIGS. 2A-2D: reduced sensitivity of MMP8$^{-/-}$ mice compared to wild type in a renal ischemia/reperfusion model. Survival (FIG. 2A) and body temperature (FIG. 2B) after 45 minutes ischemia; survival (FIG. 2C) and body temperature (FIG. 2D) after 60 minutes ischemia.
Figure 2B:
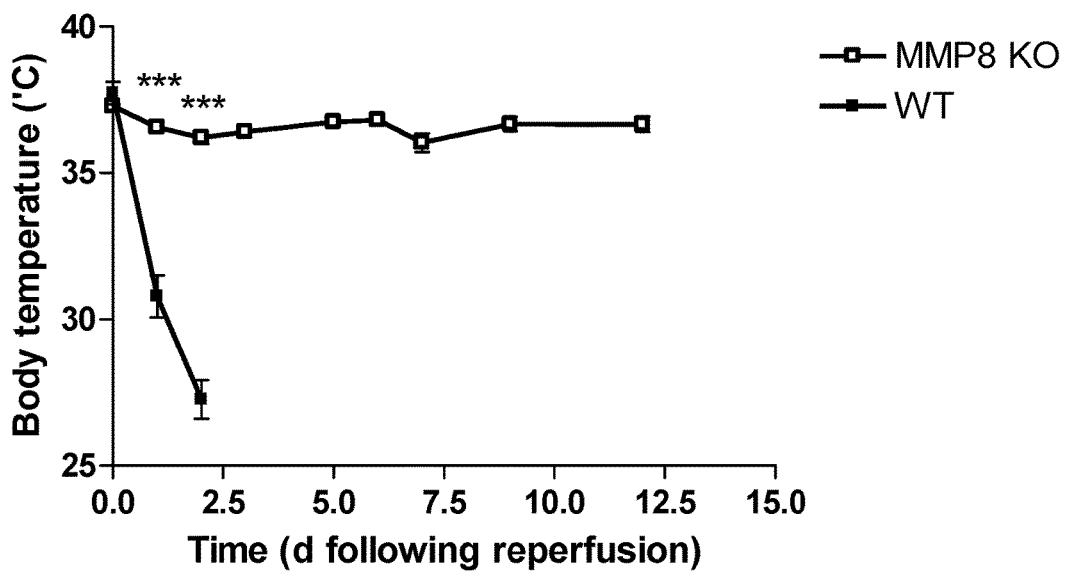
Figure 2C:
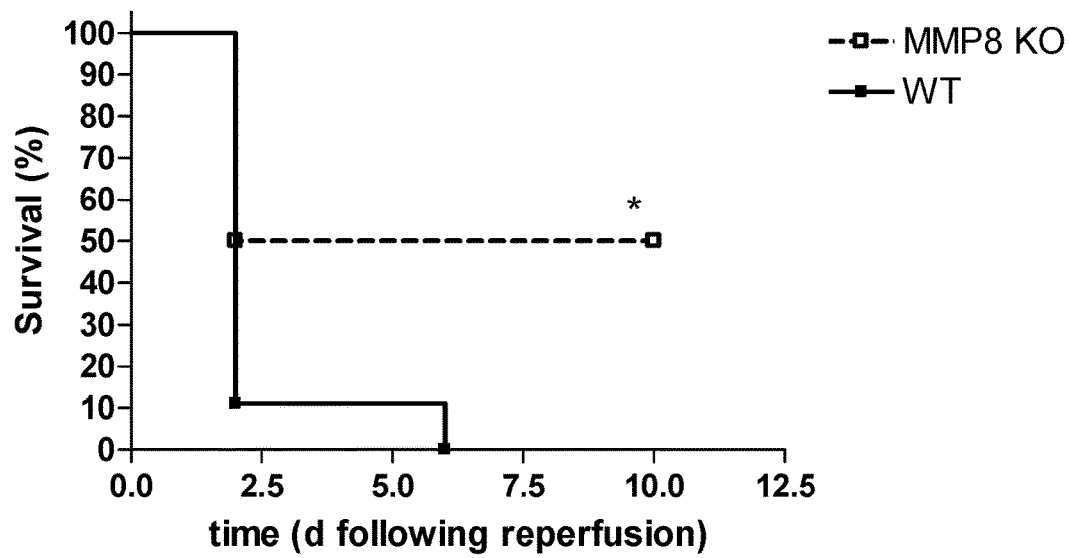
Figure 2D:
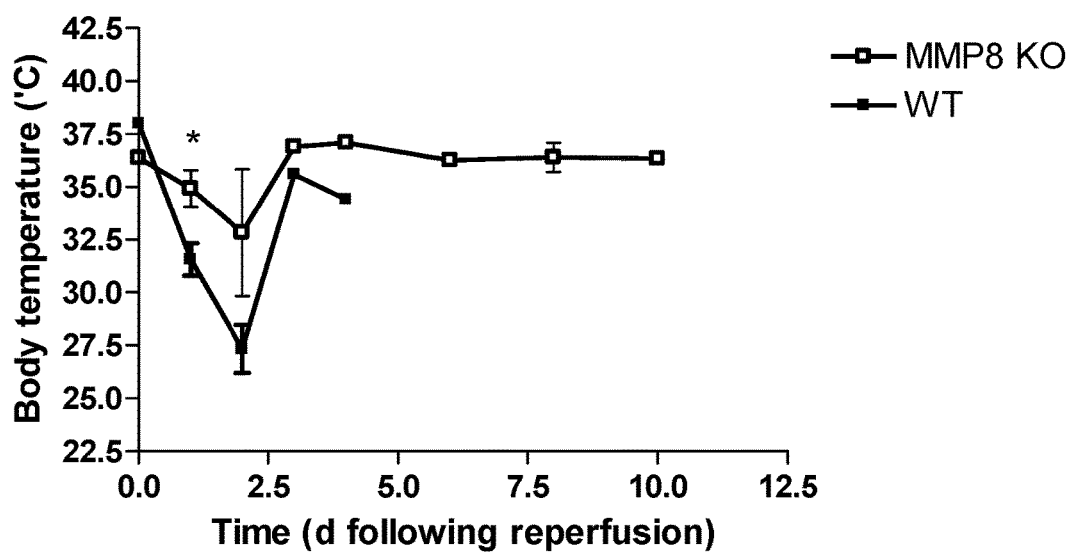
Figure 3:
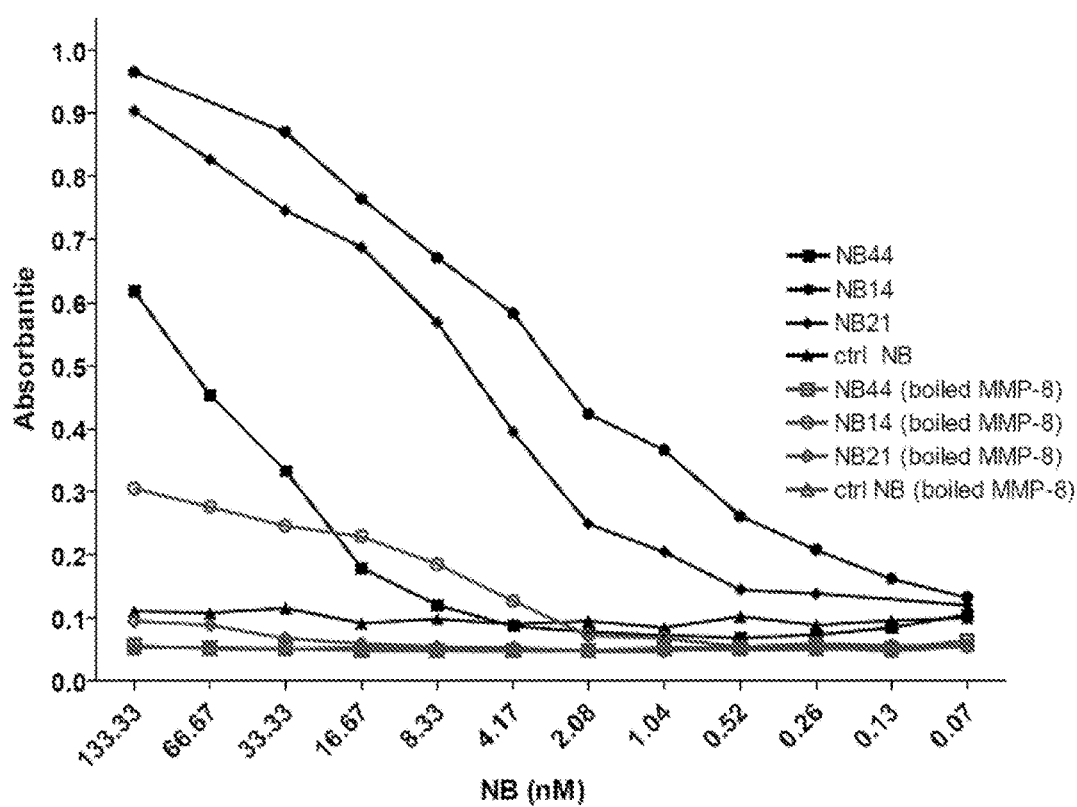
FIG. 3: Binding capacity of nanobody 14, nanobody 21, nanobody 44 and an irrelevant control nanobody to coated MMP8, as measured in an ELISA test.
Figure 4A:
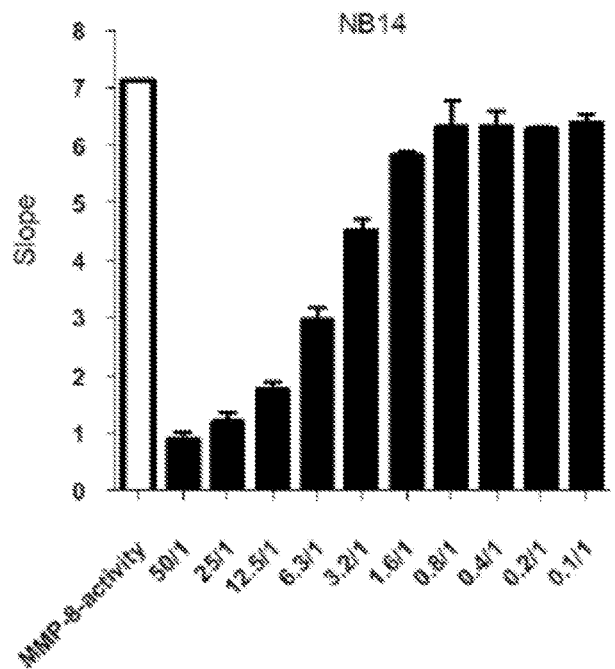
FIGS. 4A-4D: MMP8 inhibitory activity of nanobody 14 (FIG. 4A), nanobody 21 (FIG. 4B), nanobody 44 (FIG. 4C) and an irrelevant control nanobody (FIG. 4D) as measured by the ENZCHECK® test.
Figure 4B:
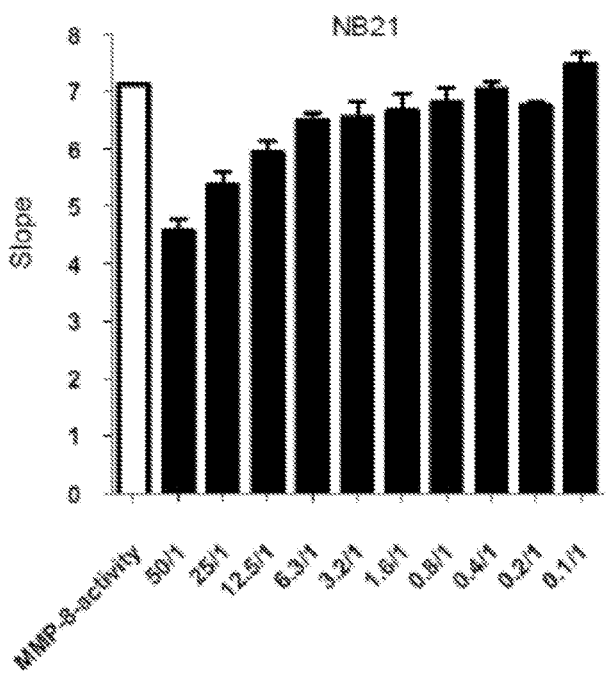
Figure 4C:
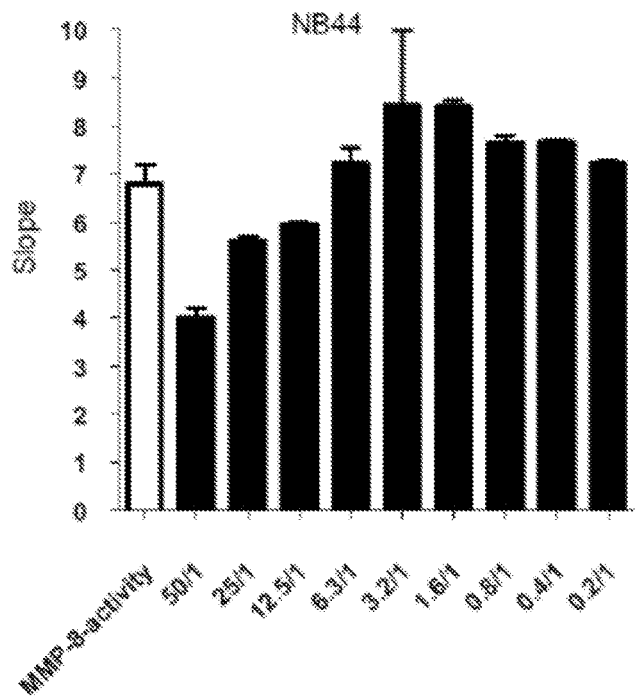
Figure 4D:
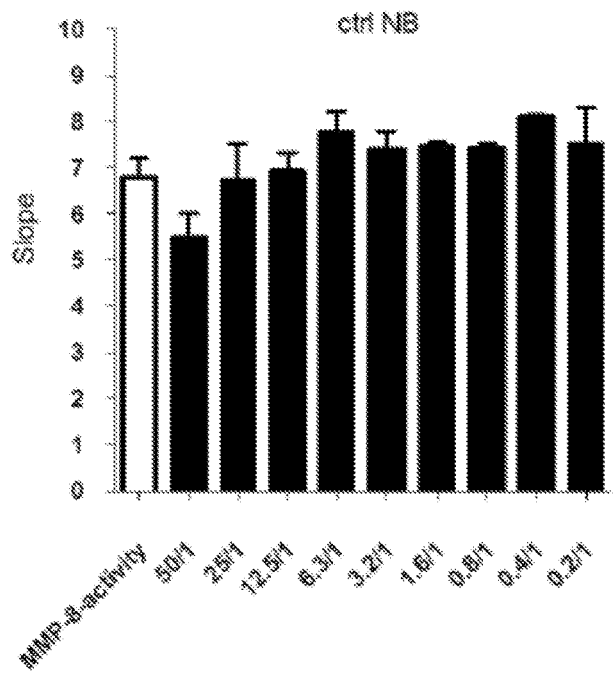

MMP-8$^{-/-}$ mice, with a C57BL/6J genetic background, and wild type mice were housed in an SPF animal facility. Males (8 weeks old) were used. All experiments were approved by the ethics committee of Ghent University. Renal ischemia was induced in isoflurane anesthetized mice by occluding the left renal pedicle for 45 min or 1 h using a vessel clip (Aesculap), and the right kidney was removed. Sham operated animals received identical treatment except for the clamping of the left renal pedicle. After 45 min of ischemia, all wild type animals died within 3 days after reperfusion, while none of the MMP-8$^{-/-}$ mice succumbed over a period of 2 weeks (FIG. 2A). 24 h after reperfusion, clear hypothermia can be observed in wild type animals, while MMP-8$^{-/-}$ mice only show a minor drop in body temperature (FIG. 2B). After 1 h of ischemia, all wild type animals died within days after reperfusion, while only half of MMP-8$^{-/-}$ mice succumbed (FIG. 2C). 24 h after reperfusion, significantly less severe hypothermia is observed in MMP-8$^{-/-}$ mice compared to wild type mice.

Example 3 isolation of MMP8 Nanobodies and Evaluation of the MMP8 Binding Capacity

MMP8 nanobodies were generated at the VIB Nanobody Service Facility. An alpaca was immunized by consecutive injections of mMMP8-CDS2 (the catalytic domain of mouse MMP8 fused to a Strep2 tag). A VHH library of about 2×10$^8$ independent transformants was constructed and screened for the presence of mMMP8-CDS2-specific nanobodies. Antigen-specific phages were isolated by four consecutive rounds of polyclonal phage ELISA using solid-phase coated mMMP8-CDS2, a process named panning. Approximately 50% (105 out of 190) of the clones tested contained mMMP8-CDS2-specific VHHs in their periplasmic extracts. From the 32 positive colonies isolated from the third panning, eight different nanobodies were selected. Recloning the nanobodies in the pHEN6c vector fused their N-termini to the PelB leader sequence, which directs them to the periplasmic space of the Escherichia coli expression host. Following expression, the nanobodies were purified by means of their C-terminal hexa-histidine tag, by ion exchange and subsequently by gel filtration. All purification steps are performed in LPS-free conditions. By ELISA, different nanobody concentrations are allowed to interact with solid-phase coated mMMP8-CDS2 (100 ng). Nanobody concentrations ranged from 68 ng (0.68/1 NB/MMP8 mol/mol ratio) till 0.04 ng (0.0003/1 NB/MMP8 mol/mol ratio). ELISA was done using native and heat denatured mMMP8-CDS2, which allows comparison of the binding strength for native and denatured MMP8. The trend in strength of binding to native recombinant mouse MMP8 was nanobody 14>nanobody 21>nanobody 44. No binding of irrelevant control nanobody to recombinant mouse MMP8 could be seen. Significantly reduced strength of binding of all nanobodies to denatured mouse MMP8 was seen.

Example 4

Inhibitory Activity of the MMP8 Nanobodies

As proteolysis of short peptide substrates may not reflect the in vivo activity on natural substrates, we made use of a protein substrate to determine MMP8 activity. To investigate the nanobodies' capacity to inhibit MMP8 activity, we used the gelatin cleavage properties of MMP8. For this we made use of the ENZCHECK® test (Invitrogen). Fluorescently labeled gelatin is added to preincubated active mMMP8-CDS2 and inhibitor (nanobody) according to the manufacturer's instructions. Briefly, 800 ng active mMMP8-CDS2 was incubated for 1 h with different nanobody concentrations, ranging from 20 µg (17/1 NB/MMP8 mol/mol ratio) till 140 ng (0.12/1 NB/MMP8 mol/mol ratio). Following incubation, 0.5 µg of gelatin was added, and conversion of the fluorescent substrate is followed for 2 h. MMP8 activity is determined as the slope of fluorescence over time. No inhibition of MMP8 activity is observed by irrelevant control nanobody. So far, nanobody 14 has the highest inhibitory potency, while nanobody 21 and nanobody 44 show only minor MMP8 inhibition.

REFERENCES

Angus, D. C., et al. Epidemiology of severe sepsis in the United States: analysis of incidence, outcome, and associated costs of care. Crit Care Med 29, 1303-1310 (2001).

Cauwe, B., Van den Steen, P. E. & Opdenakker, G. The biochemical, biological, and pathological kaleidoscope of cell surface substrates processed by matrix metalloproteinases. Crit Rev Biochem Mol Biol 42, 113-185 (2007).

Cohen, J. The immunopathogenesis of sepsis. Nature 420, 885-891 (2002).

Esper, A. M., et al. The role of infection and comorbidity: Factors that influence disparities in sepsis. Crit Care Med 34,2576-2582 (2006).

Gross, J. & Lapiere, C. M. Collagenolytic activity in amphibian tissues: a tissue culture assay. Proc Natl Acad Sci USA 48, 1014-1022 (1962).

Hulboy, D. L., Rudolph, L. A. & Matrisian, L. M. Matrix metalloproteinases as mediators of reproductive function. Mol Hum Reprod 3, 27-45 (1997).

Malemud, C. J. Matrix metalloproteinases (MMPs) in health and disease: an overview. Front Biosci 11, 1696-1701 (2006).

Page-McCaw, A., Ewald, A. J. &Werb, Z. Matrix metalloproteinases and the regulation of tissue remodeling. Nat Rev Mol Cell Biol 8, 221-233 (2007).

Parks, W. C., Wilson, C. L. & Lopez-Boado, Y. S. Matrix metalloproteinases as modulators of inflammation and innate immunity. Nat Rev Immunol 4, 617-629 (2004).

Pulskens, W. P., Teske, G. J., Butler, L. M., Roelofs, J. J., van der Poll, T., Florquin, S. And Leemans, J. C. Toll-like receptor 4 coordinates the innate immune response of the renal ischemia/reperfusion injury. PLoS One, 3, e3596 (2008).

Roy, R., Zhang, B. & Moses, M. A. Making the cut: protease-mediated regulation of angiogenesis. Exp Cell Res 312, 608-622 (2006).

Sternlicht, M. D. & Werb, Z. How matrix metalloproteinases regulate cell behavior. Annu Rev Cell Dev Biol 17, 463-516 (2001).

Tramontano, A., Bianchi, E., Venturini, S., Martin, F., Pessi, A and Sollazzo, M. The making of the minibody: an engineered beta-protein for the display of confromationally constrained peptides. J. Mol. Recognition 7, 9-24 (1994).

Van Lint, P. & Libert, C. Matrix metalloproteinase-8: cleavage can be decisive. Cytokine Growth Factor Rev 17, 217-223 (2006).

van Ruler, O., Schultz, M. J., Reitsma, J. B., Gouma, D. J. & Boermeester, M. A. Has mortality from sepsis improved and what to expect from new treatment modalities: review of current insights. Surg Infect (Larchmt) 10, 339-348 (2009).

Van Wart, H. E. & Birkedal-Hansen, H. The cysteine switch: a principle of regulation of metalloproteinase activity with potential applicability to the entire matrix metalloproteinase gene family. Proc Natl Acad Sci USA 87, 5578-5582 (1990).

Vincent, J. L. Drotrecogin alpha (activated): the treatment for severe sepsis? Expert Opin Biol Ther 7, 1763-1777 (2007).

Vu, T. H. & Werb, Z. Matrix metalloproteinases: effectors of development and normal physiology. Genes Dev 14, 2123-2133 (2000).

Wesolowski, J., Alzogaray, V., Reyelt, J., Unger, M., Juarez, K., Urrutia, M., Cauerhiff, A., Danquah, W., Rissiek, B., Scheuplin, F., Schwarz, N., Adriouch, S., Boyer, O., Seman, M., Licea, A., Serreze, D. V., Goldbaum, F. A., Haag, F. and Koch-Nolte, F. Single domain antibodies: promising experimental and therapeutic tools in infection and immunity. Med. Microbiol. Immunol. 198, 157-174 (2009).

The invention claimed is:

1. A matrix metalloproteinase-8 (MMP8)-inactivating antigen binding protein,
   wherein the MMP8-inactivating antigen binding protein comprises a single domain antibody that specifically binds to MMP8, and
   wherein the single domain antibody comprises the complementary determining region sequences of the camelid heavy chain antibody of SEQ ID NO: 1.

2. The MMP8-inactivating antigen binding protein according to claim 1, wherein said MMP8-inactivating antigen binding protein comprises the variable domain of the camelid heavy chain antibody (VHH) of SEQ ID NO: 1.

3. A method of producing the matrix metalloproteinase-8 (MMP8)-inactivating antigen binding protein of claim 1, the method comprising:
   utilizing a host cell transformed with a polynucleotide encoding the MMP8-inactivating antigen binding protein to produce the MMP8-inactivating antigen binding protein.

4. A method of detecting a matrix metalloproteinase-8 (MMP8), the method comprising:
   utilizing the MMP8-inactivating antigen binding protein of claim 1 to detect the MMP8.

5. An antigen binding protein that inactivates matrix metalloproteinase-8 (MMP8), the antigen binding protein comprising:
   a peptide comprising 4 framework regions and the 3 complementary determining
   region sequences of the camelid heavy chain antibody (VHH) of SEQ ID NO: 1.

6. An antigen binding protein that inactivates matrix metalloproteinase-8 (MMP8), the antigen binding protein comprising:
- a peptide comprising 4 framework regions and 3 complementary determining regions,
- wherein the antigen binding protein comprises the variable domain of the camelid heavy chain antibody (VHH) of SEQ ID NO: 1.

7. A method of producing an antigen binding protein that inactivates matrix metalloproteinase-8 (MMP8), the method comprising:
- expressing a polynucleotide encoding the antigen binding protein of claim 6 to produce the antigen binding protein.

* * * * *

SEQUENCE LISTING

```
<160> NUMBER OF SEQ ID NOS: 8

<210> SEQ ID NO 1
<211> LENGTH: 121
<212> TYPE: PRT
<213> ORGANISM: Artificial Sequence
<220> FEATURE:
<223> OTHER INFORMATION: Nanobody

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Asn Ile Gly Trp Phe Arg Gln Ala Pro Gly Lys Glu Arg Glu Arg Val
        35                  40                  45

Ser Cys Ile Ser Ser Ser Gly Gly Arg Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala His Cys Met Ala Thr Thr Glu Gly Tyr Glu Tyr Asp Tyr Trp Gly
            100                 105                 110

Gln Gly Thr Gln Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Nanobody

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Asn Ile Gly Trp Phe Arg Gln Ala Pro Gly Lys Glu Arg Glu Arg Val
        35                  40                  45

Ser Cys Ile Ser Ser Ser Gly Gly Asn Thr Asn Tyr Ala Asp Ser Val
    50                  55                  60
```

-continued

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Val Tyr Tyr Cys
                 85                  90                  95

Ala His Cys Met Ala Thr Thr Glu Gly Tyr Glu Tyr Asp Tyr Trp Gly
            100                 105                 110

Gln Gly Thr Gln Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Nanobody

<400> SEQUENCE: 3

Gln Val Gln Leu Gln Glu Ser Gly Gly Gly Leu Val Gln Pro Gly Gly
 1               5                  10                  15

Ser Leu Arg Leu Ser Cys Thr Ala Pro Gly Phe Thr Leu Asp Tyr Tyr
                 20                  25                  30

Asn Ile Gly Trp Phe Arg Gln Ala Pro Gly Lys Glu Arg Glu Arg Val
             35                  40                  45

Ser Cys Ile Ser Ser Ser Gly Gly Ser Thr Asn Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Val Tyr Tyr Cys
                 85                  90                  95

Ala His Cys Met Ala Thr Thr Glu Gly Tyr Glu Tyr Asp Tyr Trp Gly
            100                 105                 110

Gln Gly Thr Gln Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Nanobody

<400> SEQUENCE: 4

Gln Val Gln Leu Gln Glu Ser Gly Gly Gly Leu Val Gln Pro Gly Gly
 1               5                  10                  15

Ser Leu Arg Leu Ser Cys Thr Ala Ser Gly Phe Thr Leu Asp Tyr Tyr
                 20                  25                  30

Asn Ile Gly Trp Phe Arg Gln Ala Pro Gly Lys Glu Arg Glu Arg Val
             35                  40                  45

Ser Cys Ile Ser Ser Ser Gly Gly Ser Thr Asn Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Gly Val Tyr Tyr Cys
                 85                  90                  95

Ala His Cys Met Ala Thr Thr Glu Gly Tyr Glu Tyr Asp Tyr Trp Gly
            100                 105                 110

Gln Gly Thr Gln Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Nanobody

<400> SEQUENCE: 5

```
Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Asn Ile Gly Trp Phe Arg Gln Ala Pro Gly Lys Glu Arg Glu Arg Val
        35                  40                  45

Ser Cys Ile Ser Ser Ser Gly Ser Thr Asn Tyr Ala Asp Ser Val
    50                  55                  60

Lys Gly Arg Phe Thr Ile Ser Arg Asp Asn Ala Lys Asn Thr Val Phe
65                  70                  75                  80

Leu Gln Met Asn Ser Leu Lys Pro Glu Asp Thr Ala Val Tyr Tyr Cys
                85                  90                  95

Ala His Cys Met Ala Thr Thr Glu Gly Tyr Glu Tyr Asp Tyr Trp Gly
            100                 105                 110

Gln Gly Thr Gln Val Thr Val Ser Ser
            115                 120
```

<210> SEQ ID NO 6
<211> LENGTH: 121
<212> TYPE: PRT
<213> ORGANISM: Artificial Sequence
<220> FEATURE:
<223> OTHER INFORMATION: Nanobody

<400> SEQUENCE: 6

```
Gln Val Gln Leu Gln Glu Ser Gly Gly Gly Leu Val Gln Pro Gly Gly
1               5                   10                  15

Ser Leu Arg Leu Ser Cys Ser Ala Ser Gly Phe Ile Leu Asp Tyr Tyr
            20                  25                  30

Asn Ile Gly Trp Phe Arg Gln Ala Pro Gly Lys Glu Arg Glu Gly Val
        35                  40                  45

Ser Cys Ile Ser Ser Ser Gly Gly Ser Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala His Cys Met Ala Leu Thr Glu Gly Tyr Glu Tyr Asp Tyr Trp Gly
            100                 105                 110

Gln Gly Thr Gln Val Thr Val Ser Ser
            115                 120
```

<210> SEQ ID NO 7
<211> LENGTH: 118
<212> TYPE: PRT
<213> ORGANISM: Artificial Sequence
<220> FEATURE:
<223> OTHER INFORMATION: Nanobody

<400> SEQUENCE: 7

-continued

```
Gln Val Gln Leu Gln Glu Ser Gly Gly Gly Leu Val Gln Pro Gly Gly
1               5                   10                  15

Ser Leu Arg Leu Ser Cys Ala Ala Ser Val Phe Thr Leu Gly Tyr Tyr
            20                  25                  30

His Ile Gly Trp Phe Arg Gln Ala Pro Gly Lys Glu Arg Glu Arg Val
        35                  40                  45

Ser Cys Ile Ser Ser Ser Gly Gly Ser Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala His Cys Gly Ala Ala Glu Gly Tyr Asp Tyr Trp Gly Gln Gly Thr
            100                 105                 110

Gln Val Thr Val Ser Ser
            115

<210> SEQ ID NO 8
<211> LENGTH: 126
<212> TYPE: PRT
<213> ORGANISM: Artificial Sequence
<220> FEATURE:
<223> OTHER INFORMATION: Nanobody

<400> SEQUENCE: 8

Gln Val Gln Leu Gln Glu Ser Gly Gly Gly Ser Val Gln Pro Gly Gly
1               5                   10                  15

Ser Leu Arg Leu Ser Cys Ala Ala Ser Gly Phe Ser Leu Ala Tyr Val
            20                  25                  30

Ala Ile Gly Trp Phe Arg Gln Ala Pro Gly Lys Glu Arg Glu Val Phe
        35                  40                  45

Ser Cys Ile Ser Ser Ser Gly Gly Ser Thr Asn Tyr Ala Asp Ser Val
    50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ile Pro Gly Leu Arg Gly Ser Ser Cys Val Ser Asp Pro Ala
            100                 105                 110

Tyr Gly His Trp Gly Gln Gly Thr Gln Val Thr Val Ser Ser
            115                 120                 125
```